United States Patent [19]

Wong

[11] Patent Number: 5,665,330
[45] Date of Patent: Sep. 9, 1997

[54] DUAL PURPOSED DIAGNOSTIC/ THERAPEUTIC AGENT HAVING A TRI-IODINATED BENZOYL GROUP LINKED TO A COUMARIN

[75] Inventor: Sui-Ming Wong, Collegeville, Pa.

[73] Assignee: Nano Systems LLC, Collegeville, Pa.

[21] Appl. No.: 385,502

[22] Filed: Feb. 8, 1995

[51] Int. Cl.⁶ .......................... A61K 49/04; A01N 43/16; C07D 311/78
[52] U.S. Cl. .................. 424/9.44; 514/454; 514/457; 549/280; 549/289
[58] Field of Search ................... 424/9.44, 9.4, 424/9.45, 9.451, 9.453, 9.455; 514/454, 457; 549/280, 289

[56] References Cited

U.S. PATENT DOCUMENTS

| | | | |
|---|---|---|---|
| 5,100,914 | 3/1992 | Redenbach-Mueller et al. | 514/457 |
| 5,141,734 | 8/1992 | Misra et al. | 423/580 |
| 5,145,684 | 9/1992 | Liversidge et al. | 424/489 |

*Primary Examiner*—Gary E. Hollinden
*Assistant Examiner*—Michael G. Hartley
*Attorney, Agent, or Firm*—Rudman & Associates

[57] ABSTRACT

The invention provides a novel compound having the structure

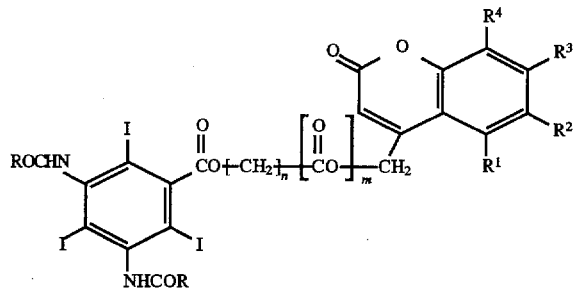

wherein R is alkyl and R1, R2, R3 and R4 are each independently OCH3, H or I and n is 0 or 1 and m is 0 or 1.

The compound is useful in a method of treating mammals either therapeutically or imaging mammals for diagnostic purposes. Useful therapeutic areas are in treating lymph nodes and tumors and diagnostic treatment is applicable to lymph nodes, tumors and in blood pool imaging. It is particularly advantageous to link an insoluble carrier molecule with a therapeutic or imaging agent to form the structure above. This makes the conjugate insoluble and thus amenable to forming nanoparticles.

14 Claims, No Drawings

DUAL PURPOSED DIAGNOSTIC/ THERAPEUTIC AGENT HAVING A TRI-IODINATED BENZOYL GROUP LINKED TO A COUMARIN

FIELD OF THE INVENTION

The present invention relates to novel compounds and their use in diagnostic imaging of mammals and the potential use in therapy. These compounds are useful in the treatment and diagnosis of tumor, lymph nodes and for imaging of blood pools.

BACKGROUND OF THE INVENTION

Compounds useful for diagnostic imaging and therapeutic treatment of mammals are numerous in the art. Most of these compounds are water soluble and hence, not amenable to use of nanoparticles such as described in U.S. Pat. No. 5,145,684 of Liversidge et al.

U.S. Pat. No. 5,141,734 describes a method of targeting an x-ray control agent to a specific population of cells or organs. Targeting may be accomplished by forming a complex of a radiographic label with an RME-type saccharide capable of interacting with a cell receptor. The radiopaque label may include a polyiodinated aromatic group.

U.S. Pat. No. 5,100,914 describes arylalkoxycoumarins wherein the aryl group can be a phenyl ring substituted with halogen. The coumarins are useful as therapeutic agents for the treatment of CNS disorders.

SUMMARY OF THE INVENTION

The present invention provides a novel compound having the formula:

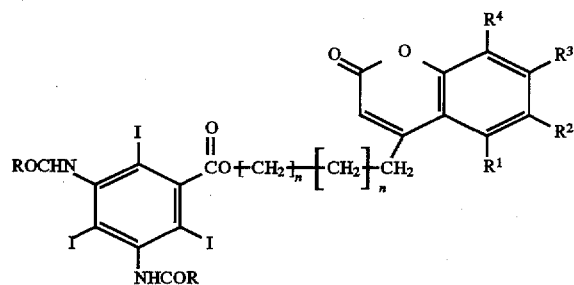

wherein R1, R2, R3 and R4 are each independently OCH3, H or I and m is 0 or 1 and n is 0 or 1.

When n and m are 0 the compound is particularly useful as a diagnostic imaging agent for mammals for lymph nodes, tumors and blood pool although it is also useful as a therapeutic agent. When an n and m are one, the compound can be early hydrolyzed by esterase and thus releasing the diagnostic and the therapeutic units as evidenced by our enzymatic hydrolysis studies of a series of diatrizoate analogues.

The invention also comprises a method of treating mammals therapeutically with compositions comprising the above compound and a method of diagnostically imaging mammals with compositions comprising the above compound. The compositions are in nanoparticulate form and should provide excellent bioavailability.

In view of the above, this invention also comprises a method of linking an insoluble carrier molecule with a soluble therapeutic or imaging agent to make the conjugate insoluble and thus amenable to forming nanoparticles.

In another embodiment of this invention, the functional state of a body organ is assessed by monitoring the rate of cleavage from the organ of the product of a carrier molecule and a diagnostic molecule.

DETAILED DESCRIPTION OF THE INVENTION

The novel compound of the invention has the formula:

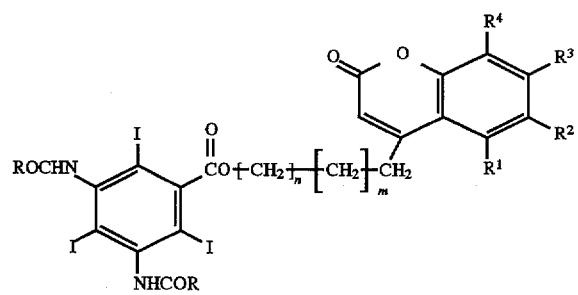

wherein $R^1$, $R^2$, $R^3$ and $R^4$ are each independently OCH$_3$, H or I and m is 0 or 1 and n is 0 or 1 and R is an alkyl comprising from 1 to 6 carbon atoms such as methyl, ethyl, isopropyl, butyl, pentyl, hexyl and the like.

When n and m are 0, the compound is useful as a therapeutic or imaging agent. When n and m are 1, the compound can be hydroylized enzymatically for assessing the functional state of a body organ.

For treating mammals therapeutically, the therapeutic component can be any water soluble agent which can form an ester bond with sodium diatrizoate, such as radiosensitizers, triapazamide or aspirins. For imaging mammals the imaging component can be any analogues of diatrizoic acids.

A nanoparticulate composition comprising the compound described above typically can contain F68, F108, T908, B20-5000, ED-BO-ED triblock copolymers, PVP, sugar surfactants as stabilizer and PEG 1450, PEG 400; DOSS as a cloud point modifier in sterilized distilled water or sterilized saline or buffers.

The nanoparticles useful in the practice of this invention can be prepared according to the methods disclosed in U.S. Pat. No. 5,145,684 and U.S. Pat. No. No. 5,318,767.

Briefly, a method for the preparation of a nanoparticle composition according to this invention includes the steps of introducing a diagnostic or therapeutic agent, a liquid medium, grinding media, and optionally, a surface modifier into a grinding vessel; wet grinding to reduce the particle size of the agent to less than about 1000 nm; and separating the particles and the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions.

A general procedure for preparing the particles useful in the practice of this invention follows. The therapeutic or diagnostic agent selected is synthesized or obtained commercially, coupled together synthetically to provide water insoluble products, and/or prepared by techniques known in the art, in a conventional coarse form. It is preferred, but not essential, that the particle size of the coarse therapeutic or diagnostic substance selected be less than about 100 m as determinedby sieve analysis. If the coarse particle size of that agent is greater than about 100 m, then it is preferred that the coarse particles of the therapeutic or diagnostic agent be reduced in size to less than 100 m using a conventional milling method such as airjet or fragmentation milling.

The coarse therapeutic/diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). it is preferred, but not essential, that the surface modifier be present in the premix. The concentration of the surface modifier can vary from about 0.1 to 90%, and preferably is 1–75%, more preferably 2–50% and most preferably 5–45 by weight based on the total combined weight of the drug substance and surface modifier. The apparent viscosity of the premix suspension is preferably less than about 1000 centipoise.

The premix can be used directly by wet grinding to reduce the average particle size in the dispersion to less than about 1000 nm. It is preferred that the premix be used directly when a ball mill is used for attrition. Alternatively, the therapeutic/diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, a planetary mill and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably less than about 1 mm. Such media desirably can provide the particles of the invention with shorter processing times and impart less wear to the milling equipment. The selection of material for the grinding media is not believed to be critical. However, media with higher density, e.g., glass (2.6 g/cm3), zirconium silicate (3.7 g/cm3), and zirconium oxide (5.4 g/cm3), are generally preferred for more efficient milling. Zirconium oxide, such as 95% ZrO stabilized with magnesia, zirconium silicate, and glass grinding media provide particles having levels of contamination which are believed to be acceptable for the preparation of therapeutic of diagnostic compositions. However, other media, such as stainless steel, titania, alumina, and 95% ZrO stabilized with yttrium, are believed to be useful. In addition, polymeric media having a density typically from 1 to 2 g/cm3 are also expected to be useful under certain milling conditions. The grinding media can be a polymeric media such as described in European Patent Application No. 600,528.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results including a high shear media mill.

An important advantage of this invention is that an insoluble compound can be formulated from a generally water soluble compound by linking the carrier (which itself can be either a imaging or therapeutic agent) which is water insoluble with the soluble therapeutic or imaging agent.

The above compounds are prepared by reacting a ditriazoat material such as sodium ditriazoate with a coumarin such as sodium methylene bromo-methoxy-coumarin. The reactions are performed under reflex by mixing the reagents in suitable solvents such as DMF, DMSO, methanol, and ethanol in the presence of a weak base such as calcium carbonate.

Despite the high water solubility of sodium ditriazoate and sodium methoxy coumarin (>1 mg/ml), WIN 67638 and WIN 67591 are sparingly soluble in water with solubility less than 0.01 mg/mL.

By water soluble is meant greater than 1 mg/ml.

The compositions of this invention can be administered by a variety of routes depending on the type of procedure and the anatomical orientation of this tissue being examined. Suitable administration routes include intravascular (arterial or venous) administation by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like. In addition to preferred applications, i.e., for blood pool, liver, spleen and lymph node imaging, the x-ray contrast compositions of this invention are also expected to be useful as an angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g.,, lymphography, lower doses, e.g., 0.5–20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and ther drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

An important feature of this invention is in functional diagnostic imaging. Conjugates, as described above, can be used to assess the functional state of various body organs. By assessing the functional state of various body organs is meant the enzymatic activity which can be measuredby the release of diagnostic agent or the carrier from enzymatic cleavage.

The above is accomplished by monitoring the product of the cleavage reaction between the carrier molecule and the diagnostic agent. For example the functional state of the liver can be monitored by the rate at which a carrier molecule is cleaved from the agent of interest and hence the rate of clearance of contrast agent from the organ. Thus, MRI, X-ray, Exterase, Amidase, DNA ASE and others can be monitored in this fashion.

The following exemplify various aspects of this invention.

EXAMPLES

Example 1 Preparation of WIN 67591

Sodium diatrizoate (2 g), 0.976 g 4-bromomethyl-6, 7 dimethoxy-coumarin and 100 mg calcium carbonate were refluxed in dimethylformamide (DMF) overnight. The reaction mixture was diluted with 10 fold volume of water to precipitate WIN 67591. The precipitate collected by filtration was further purified by successive washing with solvents, water (3 volume) followed by mathanol (3 volume) and dichloromethane (3 volume), and drying under nitrogen to afford 1.5 g WIN 67591.

WIN 67591 appeared as a single peak at retention time 5.19 min. in the HPLC chromatogram obtained with the following conditions:

Instrument HP1090

Column: RP18 (E. Merck)

Solvent: MeOH: 2% TFA (3:2)

Flow rate: 0.8 ml/min

Monitor UV wavelength: 250 nm.

Its structure was confirmed by NMR, UV and MS spectral analysis to be

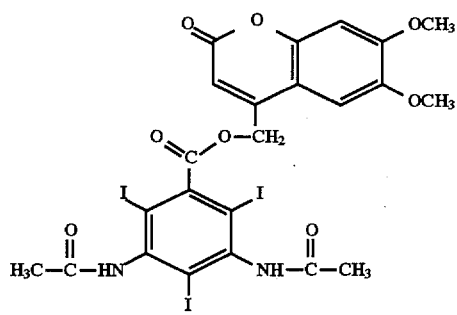

Example 2 Preparation of WIN 67638

Sodium diatrizoate (2 g) was mixed with 4-bromomethyl-7-methoxy-coumarin (0.976 g) in DMR containing 5 mg of calcium carbonate. The reaction mixture was refluxed for 3 hours and then dried under nitrogen. Successive washes of the dried powder with water, methanol and chloroform gave 1.6 g WIN 67638 which appeared as a single spot at a RF value of 0.26 on the TLC plate developed with a mixture of chloroform: methanol: TA (10:1:1). The structure of WIN 67638 was confirmed by NMR, UV and MS spectral analysis to be

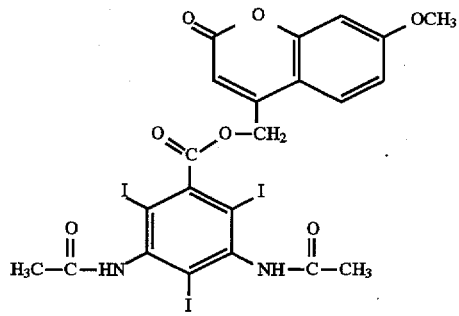

Example 3 Preparation of Nanoparticulate WIN 67591 for Lymphography 0.75 g of WIN 67591, as prepared in Example 1, was added to approximately 30 ml of 1.1 mm zirconium oxide beads and 10 ml of a solution which was 2% Tetronic 908 (wt/vol %) and 1% SA9OHCO (wt/vol %). SA9OHCO is a small sugar surfactant. The suspension was roller milled in a 60 ml jar at approximately 100 rpm for 7 days. At the end of this time, the average particle size was determined to be 192 nm by light scattering using a Zetasizer III. The suspension was removed from the beads and sent for subcutaneous injection as a lymphographic agent. CT imaging was carried out using a GE Model 9800 Instrument. Even though formulated at a low percent solids (i.e., normal formulations are 15%), this suspension gave clear enchancement of the axillary nodes of New Zealand White Rabbits at 4 hours post injection of a single 0.5 ml dose on the dorsal side of the forepaw. The imaging effect of this 5% solution of WIN 67591 is similar to that of a 15% formulation of WIN 8883 having the structure

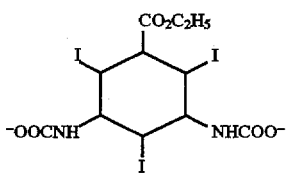

Example 4 Nanoparticulation of WIN 67591 for Blood Pool Imaging 2.85 g of WIN 67591 (19.2%) were added to 30 ml of a solution of 5.2% BASF NF Grade Tetronic 908 (wt/vol %) in sterilized distilled water and approximately 100 ml of 1.1 mm zirconium silicate beads in a 250 ml bottle. The bottle was capped and rolled at approximately 140 rpm for 7 days at which time the average particle size was determined to be 173 nm. The suspension was separated from the beads and sent for intravenous injection as a vascular x-ray contrast agent. New Zealand White rabbits were used for this study and were injected via the ear vein at a dose of 3 ml/kg. Three animals were studied for times 5, 15, 30, 60, 120 min. and 24 hours. CT scanning was carried out using a Toshiba Model TCT-900S/x at the times indicated. The results indicate that this formulation demonstrates prolonged vascular residence at times beyond 2 hours.

Example 5 Use of WIN 67591 as an Oncological Therapeutic Agent

A nanoparticulate formulation of 5% w/v WIN 67951 in 3% polyoctylphenol (Tyloxopol) was prepared by ten days roller milling following the procedures similar to that of Example 9.

The formulation was administered to mice bearing colon 33 tumor by iv injection. Analysis of the tumor tissue indicated the presence of WIN 67591 in the tumor tissue as soon as 5 minutes after injection. The drug concentration reached a maximum of 90 µg/g of tumor tissue at 6 hours and maintained at a concentration of 60 µg/g of tumor tissue for 42 hours. This concentration in the tumor tissue exceeds the average therapeutic dosage of oncologics.

This sustained accumulation of relatively high dose of WIN 67591 in the tumor tissue suggested the potential of applying this technology for oncologics, especially for the radiosentizer WIN 59705 and analogues where tumor can be visualized by the diagnostic agent unit before activation of the radiosentizer.

Example 6 Use of WIN 67591 as a Blood Pool Imaging Agent

A biodistribution study of the treatment of Example 5 was conducted by iv injections into colon 33 tumor bearing mice at 0.2 ml/animal. WIN 67591 was found to circulate in the blood for at least one hour. No dead mice were reported during the 48 hours treatment. This indicates that WIN 67591 is useful as a blood pool imaging agent.

Example 7 Nanoformulation of WIN 67591 for Biodistribution Studies

WIN 69791 as prepared in Example 1 at 5% W/V was formulated with 3% Tyloxapol by roller milling for ten days following the procedures similar to that of work example 3 and 4. The average particle size by PCS was 302 nm. The formulation was administered i.v. to colon 33 bearing mice at 0.2 ml/animal. HPLC analysis of the tumor tissue indicated prolonged blood circulation of WIN 67591 nanocrystal. As high as 700 ug (0.7% of the total dosage) WIN 67591 remained circulating in the blood 1 hour post injection. WIN 67591 was detected in the tumor tissue as early as 5 minute post injection. The drug concentration reached a maximum at 90 ug/g of tumor tissue at 6 hour post injection and maintained at a concentration of 60 ug/g in the tumor tissue for 48 hours.

I claim:

1. A compound having the structure

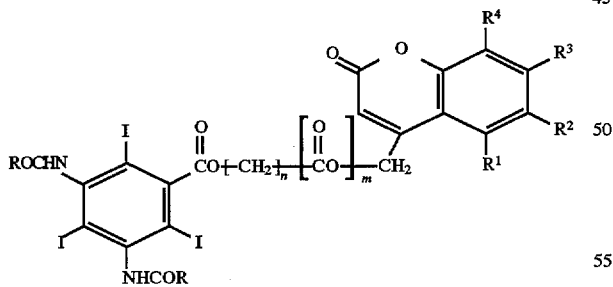

wherein

R is alkyl comprising from 1 to 6 carbon atoms;

$R^1$, $R^2$, $R^3$, and $R^4$ is each independently $OCH_3$, H or I n is 0 or 1; and m is 0 or 1.

2. The compound of claim 1 wherein;

R is $CH_3$;

$R^1$ is hydrogen;

$R^2$ is $OCH_3$ or hydrogen;

$R^3$ is $OCH_3$; and $R^4$ is hydrogen.

3. The compound of claim 1 wherein n is 0.

4. The compound of claim 1 wherein n is 1.

5. A method of diagnosing a mammal, wherein the method comprises administering to the mammal a nanoparticulate formulation comprising the compound of claim 1 and subjecting said mammal to a CT X-ray imaging procedure.

6. The method of claim 5 wherein lymph nodes are imaged.

7. The method of claim 5 wherein a tumor is imaged.

8. The method of claim 5 wherein the mammal's blood pool is imaged.

9. A nanoparticulate formulation comprising the compound of claim 1.

10. A nanoparticulate formulation comprising the compound of claim 2.

11. A nanoparticulate formulation comprising the compound of claim 3.

12. A nanoparticulate formulation comprising the compound of claim 4.

13. A compound of the structure

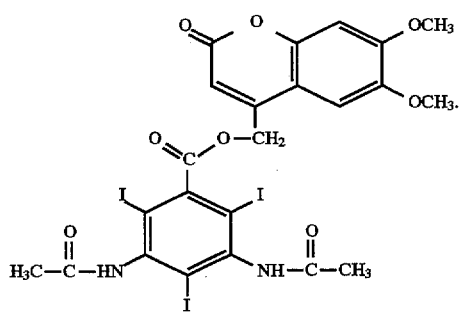

14. A compound of the structure

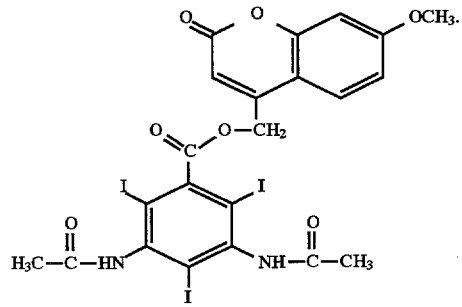

* * * * *